US006844012B1

(12) United States Patent
Forceville et al.

(10) Patent No.: US 6,844,012 B1
(45) Date of Patent: Jan. 18, 2005

(54) USE OF SELENIUM FOR TREATING PATIENTS SUFFERING FROM SYSTEMIC INFLAMMATORY RESPONSE SYNDROME (SIRS), AND COMPOSITION FOR IMPLEMENTING SAID TREATMENT

(75) Inventors: Xavier Forceville, 12 rue de Champagne, Saint Germain sur Morin (FR), 77860; Dominique Vitoux, Paris (FR)

(73) Assignee: Xavier Forceville, Saint Germain sur Morin (FR)

( * ) Notice: Subject to any disclaimer, the term of this patent is extended or adjusted under 35 U.S.C. 154(b) by 0 days.

(21) Appl. No.: 09/763,870

(22) PCT Filed: Aug. 30, 1999

(86) PCT No.: PCT/FR99/02066

§ 371 (c)(1),
(2), (4) Date: Feb. 28, 2001

(87) PCT Pub. No.: WO00/12101

PCT Pub. Date: Mar. 9, 2000

(30) Foreign Application Priority Data

Aug. 31, 1998 (FR) .............................................. 98 10889

(51) Int. Cl.[7] ...................... A61K 31/095; A61K 33/04; A61K 31/198; A61K 31/197; A61K 35/72
(52) U.S. Cl. .................... 424/702; 424/93.51; 424/630; 424/631; 424/632; 424/633; 424/634; 424/635; 424/637; 424/638; 424/641; 424/642; 424/643; 424/649; 424/DIG. 6; 514/184; 514/458; 514/474; 514/494; 514/495; 514/499; 514/500; 514/554; 514/556; 514/561; 514/562; 514/563; 514/564; 514/673; 514/706; 514/825; 514/826; 514/885; 514/888; 514/898; 514/921
(58) Field of Search ...................... 424/93.51, 630–635, 424/637–638, 641–643, 649, 702, DIG. 6; 514/184, 458, 474, 494, 495, 499, 500, 554, 556, 561–564, 673, 706, 825, 826, 885, 888, 898, 921

(56) References Cited

FOREIGN PATENT DOCUMENTS

WO    WO 96/30007    10/1996
WO    98/33495    *   8/1998

OTHER PUBLICATIONS

Chemical Abstracts 116:150492 (1992).*
Hofbauer, L. C. et al., "Selenium–induced thyroid dysfunction," Postgraduate Medical Journal, vol. 73(856), Feb. 1997, pp. 103–104.*
MEDLINE Abstract, accession No. 89114296 (1989).*
Chemical Abstracts 108:149240 (Apr. 1988).*
Chemical Abstracts 127:171274 (Sep. 1997).*
Chemical Abstracts 129:134509 (Sep. 1998).*
Medline Abstract, accession No. 89032644 (1988).*
T. Zimmerman et al., "Selensubstitution bei Sepsispatienten. Eine prospektiv randomisierte Studie.", Medizinische Klinik, Sep 15, 1997, 92 Suppl 3 P3–4.
R. Gartner et al., "Selensubstitution bei Sepsispatienten" Medizinische Klinik, 92/Suppl. 3 (12–14).
J. Borner et al., "Selensubstitution bei schweren entzunddlichen chirurgischen Krankheitsbildern sowie Verbrennungen und Verbruhungen im Kindesalter." Medizinische Klinik, Sep 15, 1997, 92 Suppl 3 P17–9.

* cited by examiner

*Primary Examiner*—John Pak
(74) *Attorney, Agent, or Firm*—Young & Thompson

(57) ABSTRACT

The invention concerns the use of at least a molecule containing selenium, in an amount corresponding to a daily dose of about 2 to 40 mg, even 80 mg of atomic selenium equivalent, on its own or combined with other synergetic molecules for controlling oxidative stress and excessive inflammatory reaction: zinc, vitamin E, vitamin C, iron binder, glutathione precursor, copper and/or copper input binder, for preparing a medicine for treating severe systemic inflammatory response syndrome, in particular any acute infectious condition endangering the patient's life whether of bacterial, parasitic, fungal or viral origin, and any condition corresponding to a severe onset of inflammatory pathology bringing about an exacerbation of cytokine secretion. The invention is applicable in human and veterinary medicine.

16 Claims, No Drawings

USE OF SELENIUM FOR TREATING PATIENTS SUFFERING FROM SYSTEMIC INFLAMMATORY RESPONSE SYNDROME (SIRS), AND COMPOSITION FOR IMPLEMENTING SAID TREATMENT

This application is a 371 of PCT/FR99/02066, filed on Aug. 30, 1999.

The present invention relates to the use of selenium for treating patients suffering from systemic inflammatory response syndrome (SIRS).

It also relates to a composition for implementing this treatment.

The role of selenium, as an oligo-element involved in many reactions in the organism, is widely known.

Thus, this element plays a major role in the intracellular antioxidant system, particularly as a component of glutathione peroxidase. In addition, selenium appears to play a direct role in the regulation of the inflammatory process.

Since the 1970's, selenium deficiency has been linked with severe cardiomyopathies, found in particular in populations living in regions of China which are deficient in selenium. The effectiveness of sodium selenite in oral form, both as a prophylactic and as a cure, against these diseases has been described.

The role of selenium in intense oxidative stress situations has been shown.

VITOUX et al. (1966, Therapeutic Uses of trace elements, Neve et al. ed., Plenum Press, New York, 127–131) have shown that the plasma concentration of selenium decreased significantly in patients admitted to intensive care units presenting a systemic inflammatory response syndrome.

However, no information was given as to the use of selenium to treat such patients.

ZIMMERMANN et al. (1997, Medizinische Klinik, 92, 3–4 suppl. III) have described, but not in detail, the results of a study on the effect of sodium selenite in patients suffering from systemic inflammatory response syndrome. In this study, the patients first received an injection of 1000 µg of sodium selenite, then 1000 µg of sodium selenite per day by continuous perfusion for twenty-eight days. The authors considered the administered dose of selenium to be optimal.

However no information was given as to the pathology of the patients treated. It is simply stated that these were patients suffering from SIRS, of which some had organ failures of unspecified nature. In addition, ZIMMERMANN et al. mentioned that the control group had a mortality rate of 40%, which is a high figure considering the type of patient treated and the stated severity index. These figures thus have low credibility and, in addition, do not agree with other data given in this article. It is thus not possible to deduce from this article what pathologies might be treated by selenium.

GARTNER et al. (Med. Klinik., 1997, vol. 92, Suppl. 3, pp. 12–14) describe the results of a clinical study in which patients suffering from systemic inflammatory response syndrome had received, in comparison with controls, an additional dose of 500 µg, 250 µg and 125 µg respectively of sodium selenite, at a frequency of one dose per day for 3 days.

BORNER et al. (Med. Klinik., 1997, vol. 92, Suppl. 3, pp. 17–19) describe a clinical study of 34 children aged from 1 to 16 years, suffering from surgical inflammatory diseases, such as extensive burns. The exogenous application of selenium was performed at a dose of 200 µg of selenium pentahydrate for patients weighing less than 15 kg, of about 500 µg for patients with weights of between 15 and 30 kg and of about 1000 µg for patients weighing more than 30 kg.

The low doses of selenium administered to the patients included in the clinical studies described by ZIMMERMANN, GARTNER and BORNER were justified by the many prejudices existing against the use of higher doses, which were generally accepted to be toxic and to present risks for the patient's life.

The PCT application no. WO 96/30007 concerns the use of mercapto and seleno derivatives as inhibitors of the enzyme nitric oxide synthase or NO synthase. This document only discloses the in vitro inhibition activity of this enzyme; such results cannot be extrapolated by a person skilled in the art in order to predict the in vivo activity of such compounds, and especially not the doses at which these compounds would be active in vivo.

Other studies describing the effect of selenium on various pathologies have been published. Thus the article of YA-JUN HU et al. (1997, Biological Trace Element Research, 56, 331–341) describes the use of selenium to reduce the toxicity of an anti-cancer product, cisplatine, in cancer patients. The patients were treated with doses of 4 mg per day of selenium, in the form of kappa-selenocarrageenan, orally.

Some of these studies show results which are conflicting and obtained on unconvincing experimental bases.

Thus, the skilled person was faced with a large number of documents stating that selenium could be used in various pathologies, but without having any real certainty as to the effect of this oligo-element, considered as toxic and pro-oxidant in the dosage regimes used in some oxidative stress situations.

Moreover some pathologies revealing a systemic inflammatory response syndrome (SIRS) are responsible for significant mortality rates, mainly in intensive care units, and severe visceral failure potentially requiring major life-support therapy.

It is thus necessary to develop a treatment which can reduce this mortality and reduce the incidence of associated visceral failures.

However, patients presenting a syndrome of the SIRS type are in a very weakened state, following an oxidative stress situation, and are considered to be poorly able to resist doses of selenium thought to be toxic, and additionally themselves pro-oxidant.

It is thus not possible for a person skilled in the art to extrapolate results obtained from patients with other pathologies to patients presenting a syndrome of the SIRS type, and to use doses of selenium considered as toxic and pro-oxidant in an oxidative stress situation.

The present invention has shown that it is possible to reduce the mortality and the incidence of visceral failures, particularly renal, respiratory, haematological (coagulation), cardiovascular, hepatic, gastro-intestinal and neurological failures resulting from a systemic inflammatory response syndrome (SIRS) by using high doses of selenium in comparison with those generally considered to be toxic by a skilled person.

It has thus been shown that good effectiveness is obtained in the treatment of syndromes of the SIRS type by treating the patients with a drug containing during the first days of the treatment a high dose of selenium, then by reducing this dose in the subsequent treatment.

The object of the present invention is thus the use of at least one molecule containing selenium, in a quantity corresponding to a daily dose of about 2 to 80 mg, and preferably 4 to 40 mg of atomic selenium equivalent, for the production of a drug for treating severe systemic inflammatory response syndrome (SIRS), or any state corresponding to a severe acute attack of an inflammatory pathology causing an exacerbation of cytokine secretion. Particularly included in this definition are any severe acute infectious condition, whether the infection is of bacterial, fungal, viral or parasitic origin.

A dose of 2 to 80 mg of atomic selenium equivalent corresponds to a dose of 0.025 to 1 mg/kg, which is the range of preferred dose in man or animals. The administration of such doses involves a strict clinical follow-up.

According to the present invention, systemic inflammatory response syndrome, or SIRS, should be understood as any pathology fulfilling the definition given by BONE et al. in 1992 during the ACCP/SCCM standardisation conference (BONE et al., 1992, Chest, 101, 1644–1655).

The invention is applicable in human and veterinary medicine.

In general, the drug administered during the initial phase of the treatment, preferably the first or the first four days of the treatment, comprises a quantity of the molecule containing selenium able drastically to reduce the inflammatory state of the patient during this initial phase of the treatment. During this period particularly, the drug is adapted to the administration of a quantity of the molecule or molecules containing selenium which is sufficient to maintain the inflammatory state of the patient or animal below a certain threshold. Thus, the quantities of the molecule or molecules containing selenium administered daily may be adapted to the particular inflammatory situation of each patient, since the level of the inflammatory response may be verified for each patient throughout the treatment.

For example, the level of the inflammatory state may be evaluated by quantifying the different cytokines in the plasma, preferably IL-6 which is currently considered as the most reliable indicator of the extent of an inflammatory situation, but also TNF-α or IL-1.

The quantity of interleukin-6 present in the serum or the plasma is preferably evaluated, for example, by a test of the ELISA type such as that distributed by MEDGENIX (Belgium).

The daily dose of the molecule or molecules containing selenium will be adapted so as to maintain the circulating level of interleukin-6 at least 30%, advantageously at least 40%, and most preferably at least 50% lower than the quantity of interleukin-6 evaluated just before the treatment by a pharmaceutical composition according to the invention. These values are given as an indication and may vary according to the pathology and, for an animal, according to the species, as a function of the clinical results obtained with the modulation of the inflammatory reaction. For monitoring the interleukin-6 levels in patients with an acute inflammatory reaction, the person skilled in the art may advantageously refer to the article by REINHART K. et al. (1996, Crit. Care Med. Vol. 24, no. 5, pages 733–742).

For quantifying the circulating levels of TNF-α, a person skilled in the art may refer to the ELISA test described by ENGELBERTS I. et al. (1991, Lancet, Vol. 338, pages 515–516).

The quantification of serum or plasma IL-1 may be performed according to the technique described by MUNOZ C. et al. (1991, Eur. J. Immunol., vol 21, pages 2177–2184).

The level of the oxidative stress state of a patient may also be evaluated by the TBA-RS test.

Finally, the level of the substances reactive to oxygen (ROS) also represents a good indicator of the inflammatory state of the patient, and may be measured for example according to the technique described by FUKUYAMA N. (1997, vol. 22 (5), pages 771–774).

This is a test for measuring the concentrations of the substances reacting with thiobarbituric acid (TBARS), present in high concentration, for example greater than 4 $\mu$/mol/litre in patients in an acute inflammatory situation, this value being given as an indication.

To perform the measurement of the concentration of TBARS, a skilled person may advantageously refer to the article by GOODE H. F. et al. (1995, Critical Care Medicine, vol. 28, no. 4, pages 646–651).

The level of peroxynitrites may be estimated by determination of nitrotyrosine, see "Quantification of protein-band 3-nitrotyrosine and 3,4-dihydroxyphenylalanine by high-performance liquid chromatography with electrochemical array detection" (HENSLEY K. Analytical Biochemistry 251, pages 187–195, 1997).

The level of the inflammatory state of the patient may also be evaluated by measuring the state of resistance of the polymorphonuclear cells to apoptosis, which is a proposed marker of the pro-inflammatory activation of these polymorphonuclear cells.

To perform this measurement, a skilled person may advantageously refer to the technique described by MARTIN S. J. et al. (1996, Cell, vol. 82, pages 349–352).

Monitoring the inflammatory situation of the patient during the treatment by a pharmaceutical composition according to the invention may also be performed by measuring the state of activation of the oxidative metabolism of the polynuclear neutrophils, such as the measurement by chemiluminescence as described for example by ALLEN R. C. et al. (1986, Meth. Enzymol., vol. 133, pages 449–493).

The drug corresponding to a daily dose of 2 to 80 mg, and preferably 4 to 40 mg, of atomic selenium equivalent, is preferably administered over a short time period, at the beginning of the treatment, with the subsequent treatment using lower doses of selenium.

The object of the present invention is therefore the use of at least one molecule containing selenium for treating SIRS in a quantity corresponding to a daily dose of about 2 to 80 mg of atomic selenium equivalent, at the beginning of the treatment, then a daily dose of about 0.5 to 2 mg of atomic selenium equivalent, in the subsequent treatment.

According to another embodiment, during the initial treatment period, increasing or decreasing doses, modulated according to the inflammatory reaction, of the molecule or molecules containing selenium may be administered so as to maintain the inflammatory state of the patient or the animal below a given level, and at a given level, which may be verified by one of the techniques described above. The molecule or molecules containing selenium may thus be administered at daily doses which may be varied and modulated during the day as a function of the monitoring of the inflammatory reaction and the oxidative stress, ranging from 2 to 80 mg of atomic selenium equivalent, i.e. from 0.025 mg/kg to 1 mg/kg of atomic selenium equivalent.

Such a drug is preferably intended for the treatment of rheumatoid polyarthritis and septic shock states such as peritonitis, pneumopathies, meningitis or bacterial septicemias and, more generally, and severe acute infectious state endangering the life of the patient, whether the infection be of bacterial, fungal, viral or parasitic origin.

It is also intended in general for the treatment of patients having a severe immuno-inflammatory reaction, associated with pancreatitis, extensive burns, multiple trauma, any type of septicemia, especially bacterial, but also in the context of severe parasitic, fungal or viral states, a major surgical operation, a surgical operation with clamping (ischemia-reperfusion), a state of shock whatever its etiology or type. The new drug may also be used in patients presenting a visceral failure. The patient may also be suffering from an alcoholic hepatopathy, cirrhosis, of whatever origin, anorexia, undernourishment, malnutrition, or AIDS or a chronic inflammatory pathology, especially intestinal.

According to a preferred embodiment, the drug is produced so as to give a daily dose of about 2 to 80 mg, preferably 4 to 40 mg, of atomic selenium equivalent, during the first day, and optionally the second, third and fourth days of treatment.

It is also advantageously produced so as to give a daily dose of about 0.5 to 2 mg of atomic selenium equivalent for 1 to 20 days and, preferably, from 1 to 10 days during the subsequent treatment, i.e. 0.025 to 1 mg/kg and, preferably, 0.05 to 0.5 mg/kg.

The molecule containing selenium may be any pharmacologically acceptable molecule. It may be a selenium salt, such as a selenite or selenate of inorganic selenium, or an organic selenium, for example selenocysteine, selenomethionine, selenodiglutathione, selenomethyl selenocysteine, dimethyl selenoxide, selenocystamine, selenated yeasts or synthetic chemicals containing one or more atoms of selenium. It is preferably sodium selenite.

It is possible, and even sometimes advantageous, to combine different forms of selenium during the use of selenium such as proposed by the invention, in particular during the phase when the very high doses are administered (from 0.025 or 0.05 to 1 mg/kg).

Sodium selenite is the preferred form but other forms of selenium may be used in combination, such as selenocysteine, selenoglutathione or other a selenium compounds.

The use of a mixture of several selenium compounds may allow more specific modulation of such aspect of the reaction of the organism during a severe SIRS by thus taking advantage of the effect of a selenium compound present in the mixture on the specific aspect to be treated: oxidative stress, NO synthesis, activation of NFKB and other transcriptional factors, secretion of pro- and anti-inflammatory cytokines, adhesins, activation of different cascades (arachidonic acid, coagulation, complement, etc.), activation of the polymorphonuclear cells and other phagocytic cells, initial resistance to apoptosis of these phagocytic cells, endothelial apoptosis and secondary visceral tissue. For example, although sodium selenite seems in general the most appropriate, for the control of certain components of the systemic inflammatory reaction such as, particularly, to modulate the action on apoptosis, it is possible to combine it with other selenium compounds.

Without wishing to be bound by any particular theory, the applicant is of the opinion that the selenium acts on target sites such as the glutathione peroxidase and selenoprotein P (vessel walls), so as drastically to reduce, at the daily quantities of atomic selenium equivalent according to the invention, the adverse effects and the level of Reactive Oxygen Species (ROS), and thus the consequences, of an oxidative stress and excessive oxidative stress for the patient or animal. The applicant also considers that the selenium causes a modulation of the concentration of intracellular peroxides, notably by its action on glutathione peroxidase, inducing a limitation of the activation of some transcription factors, and especially NFKB, which could lead to a reduction of the production of NO synthase and certain cytokines such as IL-6.

In addition, the applicant considers, without wishing to be bound by such a theory, that selenium at very high doses induces a significant apoptosis of some cells involved in the inflammatory response of the host, particularly the polynuclear neutrophils or by modification of their cell cycle. These actions on these cells are likely considerably to reduce the inflammatory state of the patient or animal, at least at the high daily doses of atomic selenium equivalent recommended. In contrast, at more moderate doses, although still high compared to the doses currently considered as usable, particularly in an oxidative stress situation, the selenium could reduce the harmful apoptosis of severe inflammatory states (endothelial cells, visceral tissue cells), in particular by the reduction in extra- and intracellular oxidative stress which it causes.

Also, when selenium compounds are used in accordance with the invention, they could exercise, when administered at very high doses, a direct antibacterial (bactericidal), antiparasitic, antiviral or antifungal action.

In consequence, a drug according to the invention advantageously contains, in combination with a therapeutically effective quantity of the molecule or molecules containing selenium, a therapeutically effective quantity of at least one compound able to inhibit oxidative metabolism or to reduce the inflammatory reaction.

The invention thus has the further object of the use of at least one molecule of selenium such as defined above, in combination with an effective quantity of at least one non-selenium compound inhibiting oxidative metabolism or acting against the consequences of oxidative stress or inhibiting the inflammatory reaction.

Various compounds inhibiting oxidative metabolism or strengthening the defences of the organism against oxidative stress may be used, in a drug according to the invention, in combination with at least one molecule containing selenium.

According to a first embodiment, a drug according to the invention comprises, in combination with the molecule or molecules containing selenium, vitamin E, optionally combined with vitamin C, taking part in the protection of membranes against oxidative stress, a precursor of glutathione, known in the state of the art, such as N-acetylcysteine, the glutathione regenerating the glutathione peroxidase in its reduced form.

According to a second embodiment, the drug contains an iron chelator, such as desferioxamine, able to reduce the production of peroxides. Desferioxamine is advantageously present in the drug for a daily dose of between 5 and 100 mg/kg. The drug may also contain a copper chelator, to exercise the same effect.

According to a third embodiment, a drug according to the invention contains, in combination with the molecule or molecules containing selenium, a therapeutically effective quantity of zinc or copper.

According to a fourth embodiment, the copper chelator and the copper are separately included in the drug, for delayed release over time. A combination of the molecule or molecules containing selenium with a copper chelator is advantageously used at the beginning of the treatment, then a combination of the molecule or molecules containing selenium with copper is used for the subsequent treatment.

Such a drug may comprise, in addition to the molecule or molecules containing selenium, vitamin E, vitamin C or zinc, or any other molecule with antioxidant activity, and which is pharmacologically compatible with the molecule containing selenium. The addition of these vitamins or this metal potentiates the effect of the selenium.

As an indication, a drug, or a pharmaceutical composition, may contain a quantity of vitamin E optionally combined with vitamin C at a daily dose of between 20 and 2000 mg of each vitamin.

A drug or a pharmaceutical composition according to the invention may additionally contain zinc at a daily dose of between 5 and 50 mg, or any other essential oligo-element.

The drug advantageously contains copper at a daily dose of between 1 and 10 mg/kg.

The drug advantageously contains N-acetylcysteine at a daily dose of between 50 and 500 mg/kg/d.

The drug preferably contains an inflammatory reaction inhibitor, for example gold at a daily dose of between 25 and 300 mg/kg.

In the case of renal insufficiency, the administration of a urinary elimination chelator, such as desferioxamine, is preferably combined with extra-renal purification by continuous hemodiafiltration or by extended hemodialysis.

According to a fifth embodiment, a drug according to the invention comprises several compounds selected from compounds which are inhibitors of oxidative metabolism and compounds reducing or inhibiting the inflammatory reaction.

The drug is preferably prepared in an injectable or perfusable pharmaceutical form or for enteral administration. It may however be in any form which allows the administration of the molecule or molecules containing selenium and the effective treatment of the SIRS.

This drug may be administered by the parenteral route, preferably by intravenous, also by subcutaneous, intramuscular, and also by intraperitoneal, enteral or oral routes.

This drug is preferably intended as curative. It may however be administered preventatively, particularly before a major surgical operation, especially vascular surgery, so as to limit the oxidative stress.

Such a drug or pharmaceutical composition may contain pharmaceutically acceptable excipients, in addition to the molecule or molecules containing selenium. In the form of a perfusion, it may contain between about 1.3 mg/l and 800 mg/l of atomic selenium equivalent.

The present invention is illustrated, without in any way being limited, by the following examples.

EXAMPLE 1

A patient aged 51, 75 kg, chronic alcoholic with no history of icteroascitic, hemorrhagic or encephalopathic compensation, was admitted to postoperative intensive care with generalized purulent peritonitis from colonic perforation during an attack of diverticular sigmoiditis.

His initial hemodynamics were maintained by perfusion. He was intubated-ventilated under sedation with a $FiO_2$, slightly increased, of 50%. There was a moderate renal insufficiency. An adapted empirical antibiotic therapy was begun, and modified after 48 hours in view of the antiobiograms. At 24 hours his severity indexes were IGS II 29, APACHE II 17 and SOFA score was 5. One day after the operation, the situation worsened rapidly with onset of a state of shock with lactic acidosis 5 μmol/l requiring administration of dopamine then rapidly noradrenaline up to 4 mg/h (0.9 μg/kg/min). There was a deterioration of his respiratory state requiring increase of the $FiO_2$ because of the onset of an acute adult respiratory distress syndrome (ARDS). As soon as the necessity of noradrenaline administration was recognized, a treatment with sodium selenite by continuous administration was begun at a dose of 4 mg of atomic selenium equivalent over the first 24 hours, followed by continuous administration of sodium selenite at a dose of 1 mg of atomic selenium equivalent for 10 days.

This treatment had the effect of limiting the extent of this vasoplegic shock condition, thus avoiding early death. This treatment also resulted in limiting the extent of visceral failure. The progress was marked by the outcome of a renal insufficiency with continued diuresis, but not requiring dialysis. Ventilation at $FiO_2$ 70% was very transiently necessary because of a rapidly resolved ARDS. The administration of noradrenaline was progressively withdrawn in three days. The lactic acidosis regressed rapidly. There was no appearance of disseminated intravascular coagulation, the platelet level remaining higher than 150 000 platelets/$mm^3$. No postoperative nosocomial infection was observed, and in particular no nosocomial pneumopathy. Nor was there any abdominal complication. This patient left intensive care 10 days after the operation.

He returned for a consultation 3 months afterwards. He then recommenced his working career and his normal lifestyle.

EXAMPLE 2

A female patient aged 35, depressive, anorexic, 51 kg and 1.75 m tall, was admitted on a tentative diagnosis of drug-induced suicide with ingestion of a large amount of analgesics and sedatives. The diagnosis was rapidly changed to generalized purulent peritonitis from a perforated gastric ulcer. She was transferred to postoperative intensive care. There was also a shock condition requiring perfusion and introduction of catechol amines as noradrenaline and dolbutamine; lactic acidosis at 6 μmol/l. Antibacterial and antifungal antibiotic therapy was performed. Diuresis was maintained under diuretics. One hour after the start of noradrenaline administration, a treatment with sodium selenite by continuous administration was begun at a dose of 4 mg of atomic selenium equivalent over the first 24 hours, followed by continuous administration of sodium selenite at a dose of 1 mg of atomic selenium equivalent for 10 days. At 24 hours the severity indexes were IGS II 44, APACHE II 35. The SOFA score was 8.

Progress was initially favorable with regression of the shock condition in 24 hours. There were no significant visceral failures, return of diuresis (creatinine clearance at 40), ventilation $FiO_2$ 60%, no PEP (positive expiration pressure), no coagulation problems except a platelet level of 50%. Onset of two atelectasia attacks requiring fibroaspiration. Early enteral feeding was installed.

Eight days after the operation, there was a persistence of a purulent discharge in the drains. Abdominal scanning showed a sub-hepatic gathering, without free peritoneal effusion. A puncture under scanner was performed to drain this gathering. Bacteriological tests on the free pus revealed colonies of *Hafnia alvei* and *Candida albicans*; the antibiotic therapy was modified according to the antibiogram.

Twelve days after the operation, a nosocomial pneumopathy from hemolytic alpha *Streptococcus* arose (diagnosed by fibroscopy with a protected telescopic brush and brochoalveolar washing). An empirical antibiotic therapy against gram positive cocci was installed, then adapted to the antibiogram. Extubation was performed 20 days after the operation. Extensive physiotherapy was necessary to avoid reintubation.

This patient was transferred to convalescent care for continuance of renutrition on the 35th day. She returned for consultation after 3 months. Her weight had risen to 56 kg. Psychotherapy was begun.

EXAMPLE 3

A patient aged 57, presenting major alcohol-tobacco addiction (more than 1 liter of wine per day, 2 packets of cigarettes per day), chronic BPCO respiratory insufficiency, stage 2 arteritis of the lower limbs and deterioration in general health for several months with a productive cough, was transferred to intensive care after a short stay in general medicine. At admission there was a respiratory distress requiring emergency intubation-ventilation. Blood gases confirmed major respiratory acidosis. The patient was feverish. There was a hyperleucocytosis of 24 000 leucocytes of which 88% were polymorphonuclear cells. Blood pressure was stable under perfusion, however there were blotches on the knees. There were no coagulation problems nor renal insufficiency. At 24 hours IGS II was 41, APACHE II 26, and SOFA score 8. Lung samples taken by protected telescopic brush and brochoalveolar washing confirmed the diagnosis of community-acquired pneumonia: 47% of cells infected, *Haemophilus influenza* β-lactamase negative and wild-type streptococcal anginosis. Dual antibiotic therapy was started which should prove effective against these organisms. Thoraco-abdominal scanning showed a large liquid gathering within the pulmonary parenchyma of the right lower lobe, appearing to fistulize in the pleural with pleurisy. The abdominal scan also revealed the existence of a thrombosed aneurism of the sub-renal abdominal aorta.

The immediate development was marked by a rapid deterioration of his respiratory state with necessity of ventilation at $FiO_2$ 100%, PEP 8. In addition, very substantial perfusion was necessary with measurement of pressure by right catheterization. Dopamine had to be administered at 10 μg/kg/min. After 8 hours dopamine administration, a treatment with sodium selenite by continuous administration was begun at a dose of 4 mg of atomic selenium equivalent over the first 24 hours, followed by continuous administration of sodium selenite at a dose of 1 mg of atomic selenium equivalent for 10 days.

After increase of the dopamine to 20 μg/kg/min and addition of adrenaline at 1 mg/h, the hemodynamics seemed to stabilize. The hyperlactatemia increased in parallel up to 10 μmol/l, then reduced as from the second day. Progress towards a fatal shock condition was thus avoided. At the respiratory level, treatment with nitrogen monoxide (NO) was started at 10 ppm. Diuresis was maintained under diuretics. There was a thrombopenia at 7500 platelets/mm$^3$ combined with a lengthening of the coagulation time and an increase in fibrin degradation products, indicating a moderate CIVD. Drainage of the purulent pleurisy was instituted.

As from the second day a progressive improvement of the situation was observed, both respiratory and hemodynamic. The drainage allowed complete evacuation of the pleurisy with drainage of the pulmonary abscess. The catechol amines were withdrawn on the fifth day. Extubation was performed on the sixth day. The patient was transferred back to pneumology on the fifteenth day for continuing exploration and treatment of his respiratory insufficiency.

This patient was seen in consultation 3 months afterwards. A dental abscess was treated. A return to normal work is under way. The patient does not have oxygenation at home.

These results are in agreement with those obtained over a larger series, showing a clear improvement of the prognosis of patients treated with high doses of selenium compared with those having received a placebo.

By IGS II should be understood the simplified severity index II defined by LE GALL et al. in 1993 (A New Simplified Acute Physiology Score) [SAPS II] Based on a European/North American Multicenter Study, JAMA, 1993; 270:2957–2963), by APACHE II (Acute Physiology and Chronic Health Evaluation II) the severity index defined by W. A. KNAUS et al. (APACHE II: A severity of disease classification system. Crit. Care Med. 1985; 13: 818–829), and by SOFA score, the score of visceral failure defined by J. L. VINCENT et al. (The SOFA [Sepsis-related Organ Failure Assessment] score to describe organ dysfunction/failure. Intensive Care Med. 1995; 22:707–710).

What is claimed is:

1. A method for treating an adult patient suffering from severe systemic inflammatory response syndrome, comprising:

administering to said patient an effective amount of a composition comprising at least one molecule containing selenium, wherein said effective amount is a daily dose of a selenium composition containing about 0.025 to 1 mg/kg of bodyweight of atomic selenium, and wherein said molecule containing selenium is selected from the group consisting of a selenium salt, selenocysteine, selenomethionine, selenodiglutathione, selenomethyl selenocysteine, dimethyl selenoxide, selenocystamine and selenated yeasts.

2. The method according to claim 1, wherein said patient is treated for a severe systemic inflammatory response selected from the group consisting of peritonitis, pneumopathies, meningitis and bacterial septicemias in a septic shock state.

3. The method according to claim 1, wherein said patient is treated for a severe systemic inflammatory response selected from the group consisting of bacterial infections, parasitic infections, fungal infections, viral infections and rheumatoid polyarthtritis.

4. The method according to claim 1, wherein said selenium is in the form of sodium selenite.

5. The method according to claim 1, wherein several molecules containing selenium are used.

6. The method according to claim 1, wherein said selenium is administered by a parenteral route, intraperitoneal route or oral route.

7. The method according to claim 1, wherein said composition further comprises a non-selenium compound which inhibits an oxidative metabolism or inflammatory reaction.

8. The method according to claim 7, wherein said associated non-selenium compound is selected from the group consisting of vitamin E, vitamin C, a glutathione precursor, an iron chelator, a copper chelator, copper and zinc.

9. The method according to claim 7, wherein said composition further comprises gold to inhibit an inflammatory reaction.

10. A method for treating an adult patient suffering from severe systemic inflammatory response syndrome or any state corresponding to a severe acute attack of an inflammatory pathology causing an exacerbation of cytokine secretion, comprising:

administering in a first treatment to said patient an effective amount of at least one molecule containing selenium, wherein said effective amount is a daily dose of a selenium composition containing about 0.025 to 1 mg/kg of bodyweight of atomic selenium, followed by further administering to said patient a subsequent treatment of an effective amount of at least one molecule containing selenium, wherein said effective amount in said second treatment is a daily dose of a selenium composition containing about 0.00625 to 0.025 mg/kg of atomic selenium, and wherein said molecule containing selenium is selected from the group consisting of a selenium salt, selenocysteine, selenomethionine, selenodiglutathione, selenomethyl selenocysteine, dimethyl selenoxide, selenocystamine and selenated yeasts.

11. The method according to claim 10, wherein said patient is treated for a severe systemic inflammatory response selected from the group consisting of peritonitis, pneumopathies, meningitis and bacterial septicemias in a septic shock state.

12. The method according to claim 10, wherein said patient is treated from a severe systemic inflammatory response selected from the group consisting of bacterial infections, parasitic infections, fungal infections, viral infections and rheumatoid polyarthtritis.

13. The method according to claim 10, wherein said first treatment is administered during a time period between a first day to fourth day of the method, and said subsequent treatment is administered 1 to 20 days after said first treatment.

14. A method for treating an adult patient suffering from severe systemic inflammatory response syndrome comprising:

administering to said patient an effective amount of a composition comprising at least one molecule containing selenium, wherein said effective amount is a daily dose of selenium composition providing about 2 to 80 mg of atomic selenium, and wherein said molecule containing selenium is selected from the group consisting of a selenium salt, selenocysteine, selenomethionine, selenodiglutathione, selenomethyl selenocysteine, dimethyl selenoxide, selenocystamine and selenated yeasts.

15. The method of claim 1, wherein the selenium salt is selected from the group consisting of a selenite or a selenate of inorganic selenium.

16. The method of claim 15, wherein the selenium salt is sodium selenite.

* * * * *